US010010856B2

(12) United States Patent
Tirtowidjojo et al.

(10) Patent No.: US 10,010,856 B2
(45) Date of Patent: Jul. 3, 2018

(54) EFFICIENT FIXED BED PLATFORM FOR PRODUCTION OF ETHYLENE OXIDE BY PARTIAL OXIDATION OF ETHYLENE USING CATALYST OF WIDE SELECTIVITY

(71) Applicant: THE DOW CHEMICAL COMPANY, Midland, MI (US)

(72) Inventors: Max M. Tirtowidjojo, Lake Jackson, TX (US); Christina Zarth, Hagebutten-weg (DE); Subrata Sen, Lake Jackson, TX (US); Pramod D. Patil, Lake Jackson, TX (US)

(73) Assignee: DOW TECHNOLOGY INVESTMENTS LLC, Midland, MI (US)

( * ) Notice: Subject to any disclaimer, the term of this patent is extended or adjusted under 35 U.S.C. 154(b) by 316 days.

(21) Appl. No.: 14/726,685

(22) Filed: Jun. 1, 2015

(65) Prior Publication Data
US 2015/0336064 A1 Nov. 26, 2015

Related U.S. Application Data

(62) Division of application No. 13/635,642, filed as application No. PCT/US2011/028763 on Mar. 17, 2011, now Pat. No. 9,073,034.

(60) Provisional application No. 61/314,677, filed on Mar. 17, 2010.

(51) Int. Cl.
*B01J 19/24* (2006.01)
*B01J 8/00* (2006.01)
(Continued)

(52) U.S. Cl.
CPC ............ *B01J 19/24* (2013.01); *B01J 8/0242* (2013.01); *B01J 8/0264* (2013.01); *B01J 8/0285* (2013.01);
(Continued)

(58) Field of Classification Search
CPC ............ B01J 19/24; B01J 2208/00115; B01J 2208/00123; B01J 2208/00132;
(Continued)

(56) References Cited

U.S. PATENT DOCUMENTS 3,252,505 A * 5/1966 Huebner, Jr. ........... F02C 7/105
165/7
4,630,785 A * 12/1986 Buchegger ............ B21C 47/30
242/573.7

(Continued)

FOREIGN PATENT DOCUMENTS

CN 201301294 Y 9/2009
DE 2204539 A1 8/1973

(Continued)

OTHER PUBLICATIONS

European Search Report for EP 11 712 373.7 International Filing Date Mar. 17, 2011; dated Jun. 27, 2014 (10 pages).

(Continued)

*Primary Examiner* — Huy-Tram Nguyen

(57) ABSTRACT

At least one method to efficiently produce alkylene oxide from partial oxidation of hydrocarbons using a high efficiency heterogeneous catalyst in a fixed bed enclosed within a reaction vessel, and a reaction vessel constructed to facilitate the same.

8 Claims, 13 Drawing Sheets

(51) Int. Cl.
  *B01J 8/02* (2006.01)
  *C07D 301/08* (2006.01)
  *C07D 301/10* (2006.01)

(52) U.S. Cl.
  CPC ........ *C07D 301/08* (2013.01); *C07D 301/10* (2013.01); *B01J 2208/00115* (2013.01); *B01J 2208/00141* (2013.01); *B01J 2208/00557* (2013.01); *B01J 2208/00893* (2013.01); *B01J 2208/02* (2013.01)

(58) Field of Classification Search
  CPC ...... B01J 2208/00141; B01J 2208/0015; B01J 2208/00159; B01J 2219/00076; B01J 2219/00078; B01J 2219/00081; B01J 2219/00083; B01J 2219/00085
  USPC .......................................................... 422/200
  See application file for complete search history.

(56) References Cited

U.S. PATENT DOCUMENTS

| | | | |
|---|---|---|---|
| 5,063,195 A | 11/1991 | Jin et al. | |
| 5,292,904 A | 3/1994 | Sawada et al. | |
| 6,284,398 B1 | 9/2001 | Kiryu | |
| 6,309,768 B1 * | 10/2001 | Patterson, Jr. | B01J 8/001 423/437.1 |
| 2002/0161243 A1 | 10/2002 | Zehner | |
| 2007/0203372 A1 | 8/2007 | Ramakers et al. | |
| 2008/0071100 A1 | 3/2008 | Billig et al. | |

FOREIGN PATENT DOCUMENTS

| | | |
|---|---|---|
| EP | 0339748 A2 | 11/1989 |
| GB | 472629 A | 9/1937 |

OTHER PUBLICATIONS

International Preliminary Report on Patentability for Application No. PCT/US2011/028763, International Filing Date Mar. 17, 2011; dated Jun. 20, 2012—21 pages.

International Search Report for Application No. PCT/US2011/028763, International Filing Date Mar. 17, 2011; dated Aug. 30, 2011—6 pages.

Written Opinion for Application No. PCT/US2011/028763, International Filing Date Mar. 17, 2011; dated Aug. 30, 2011—12 pages.

XP-002656919—Thomson Scientific Abastract for SU 980802 Publication date Dec. 15, 1982; 1 page.

* cited by examiner

EFFICIENT FIXED BED PLATFORM FOR PRODUCTION OF ETHYLENE OXIDE BY PARTIAL OXIDATION OF ETHYLENE USING CATALYST OF WIDE SELECTIVITY

CROSS-REFERENCE TO RELATED APPLICATIONS

This application claims priority to U.S. Non-Provisional Application Serial No. 13/635642, filed on Mar. 17, 2011, now U.S. Patent No. 9,073,034, which claims priority to International Application No. PCT/US2011/028763 filed on Mar. 17, 2011, which claims priority to U.S. Provisional Application No. 61/314,677 filed on Mar. 17, 2010, the entire contents of which are hereby incorporated by reference.

TECHNICAL FIELD

Currently, reactors for producing ethylene oxide (EO) by partial oxidation of ethylene typically make use of a single conventional fixed-bed shell-tube exchanger (FB) where the catalytic reaction occurs inside the tubes. The fabrication of this type of reactor has reached engineering and transportation limitations due to weight and size factors. It is typical in a conventional design to have 8,000-14,000 tubes with up to 2" internal diameter tubes (Dt) arranged in the shell diameter (Ds) with a Ds of 6-9 meters (M) and tube sheets approaching 1.0 ft to 2.0 ft in thickness. A reactor with an even larger Dt and Ds can theoretically be used to provide a more economically advantageous process given the continually advancing catalyst formulations that are improving average selectivity of 80% to 95% during such a reactor's life time. There is a need for a reactor configuration as an alternative platform for EO catalyst with efficiency higher than 80% that is lower in weight and provides lower pressure drop across the reactor and thus provides higher return on capital investment due to lower operating and capital cost as compared to using a conventional FB reactor.

BRIEF SUMMARY

In one embodiment, the disclosure relates to a reaction vessel for production of alkylene oxide(s) from partial oxidation of hydrocarbon using a high efficiency heterogeneous catalyst in a fixed bed enclosed within a reaction vessel shell. The reaction vessel may comprise a shell having a length and a volume that defines a catalyst bed shape having a length such that an out flow area and an in flow area over the catalyst bed length in between the out flow and in flow has an absolute ratio difference less than or equal to about 1.3 M anywhere in the reactor bed. The catalyst bed defines a process side having a selectivity greater than about 80%, and the catalyst bed has a length less than the shell length and a width that defines a volume less than the shell volume. The reaction vessel further includes a fixed bed outlet zone configured with average residence time less than or equal to about 4 seconds of the gaseous product flow from the catalyst bed over the heat exchanger to quench the undesirable side reactions involving the alkylene oxide product. The vessel also includes at least one fluid coolant enclosure heat exchanger in the vessel interior with an outside surface and an inside surface. The coolant enclosure outside surface is in contact with the catalyst bed. The coolant enclosure has an inlet and an outlet for the flow of heat transfer fluid therethrough. The coolant enclosure may further define a cooling surface area with the coolant flow cross sectional area ratio to cooling surface area much less than about 1 and where pressure in the coolant side may be higher than pressure on the process side.

In another embodiment, the disclosure relates to at least one method for producing ethylene oxide from partial oxidation of ethylene using a high efficiency ethylene oxide catalyst in a fixed bed enclosed within a shell of a reaction vessel. In one embodiment, the method may comprise introducing a sufficient amount of gaseous ethylene, oxygen, ballast gases that include, but are not limited to, methane, inert gases such as $N_2$, He, Ar and any other inert gas, and at least one catalyst promoter such as, but not limited to, $NH_3$, vinyl chloride, ethyl chloride, and others, into an in flow of the reaction vessel and flowing the ethylene, oxygen, ballast gas and promoters over an ethylene oxide (EO) catalyst bed that provides a selectivity to EO of greater than about 80%. The reaction vessel may comprise a shell having a length and a volume that defines a catalyst bed shape having a length such that an out flow area and an in flow area over the catalyst bed length in between the out flow and in flow has an absolute ratio difference less than or equal to about 1.3 M anywhere in the reactor bed. The method further includes circulating a heat transfer fluid within a coolant enclosure contained within the reaction vessel catalyst bed. The coolant enclosure defines a coolant side, and the coolant side may have a greater pressure than the process side. The coolant enclosure has an outside surface in contact with the catalyst bed, and has an inlet and an outlet for the circulation of heat transfer fluid therethrough. Generally, the coolant enclosure defines a cooling surface area with a coolant flow cross sectional area ratio to cooling surface area much less than about 1. The reaction vessel further includes a fixed bed outlet zone configured with an average residence time less than or equal to 4 seconds of gaseous product flow from the outlet of the catalyst bed over the heat exchanger to quench any undesirable side reactions involving the ethylene oxide product.

DETAILED DESCRIPTION OF THE INVENTION

Figure 1A:
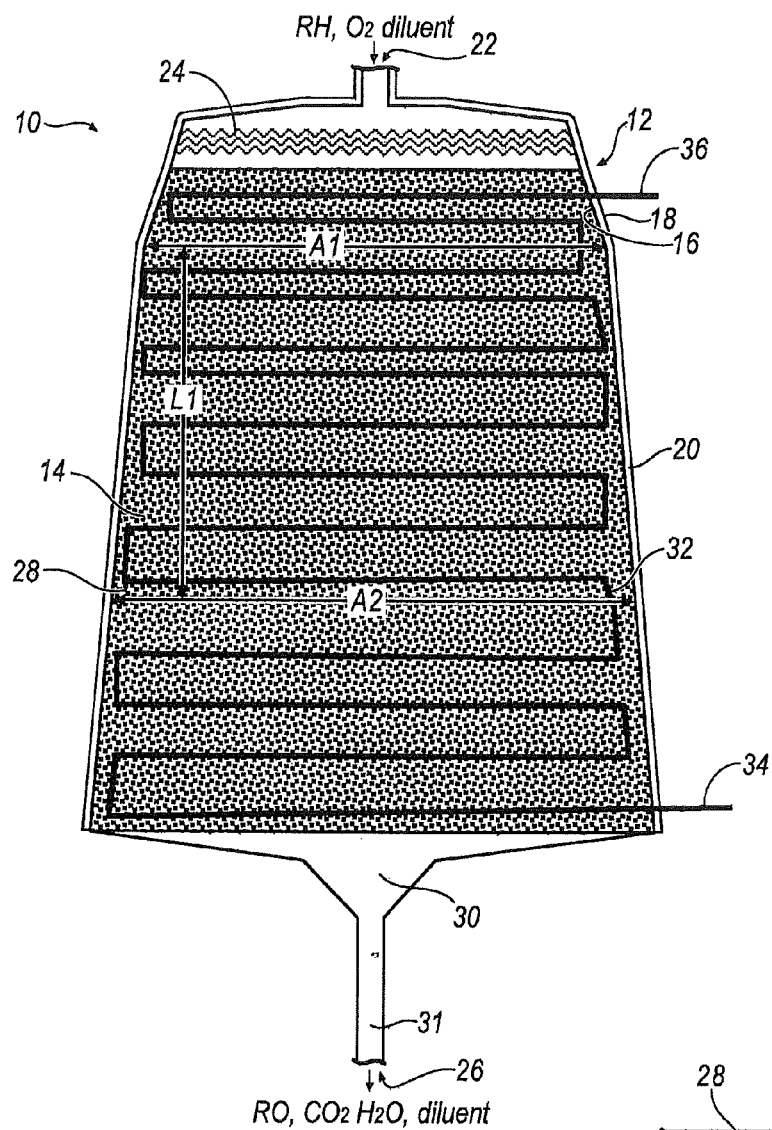
FIG. 1A is a schematic representation of a reaction vessel according to at least one embodiment.

Turning now to the drawings wherein like numbers refer to like structures, FIG. 1A is a schematic representation of a reaction vessel 10 having a shell enclosure 12 of a length and width that defines an internal space 14. The shell is a wall with an inner surface 16 and an outer surface 18, separated by an insulation layer 20. While the shell is shown schematically, those skilled in the art understand that it could be constructed in any shape desired. The shell is constructed of materials having sufficient strength to contain the internal pressures that arise as the operation of the reaction vessel as is well known in the art. The reaction vessel is further equipped with an in flow 22 for ingress of hydrocarbon or other gaseous raw materials, such as, for example ethylene, oxygen, ballast gases, and gaseous catalyst promoters, into the feed distribution device 24 and an out flow 26 for effluent gaseous products. In this regard, it is apparent to those skilled in the art that the term "ballast gases" are understood to be, but are not limited to, $CO_2$, $CH_4$, inert gasses such as $N_2$, Helium, Argon, or any other noble gas. Similarly, catalyst promoters may be, but are not limited to, ammonia ($NH_3$), especially for high selectivity catalysts, chlorides, vinyl chloride, ethyl chloride, ethane, and any other suitable gaseous promoter. The in flow and the out flow of the shell are configured to produce an exit gas velocity of from about 5 ft/s, to about 25 ft/s, upon exiting the fixed bed reaction zone within the reactor vessel before entering an outlet pipe 31. The gaseous in flow and out flow have an absolute ratio difference of inlet and outlet flow area over the catalyst bed length from about 0.8 meters to about 1.3 meters and more preferably from about 0.9 to about 1.2 meters. In one embodiment, the shell has an interior pressure during gaseous raw material ingress and gaseous effluent product egress of less than about 350 psig.

Between the in flow and the out flow, there is a catalyst bed 28 carried within the shell made of a high or low selectivity catalyst for the oxidation of the gaseous raw material, such as, for example ethylene, to ethylene oxide in a manner to be hereinafter described. The catalyst bed is also known as the process side of the reactor and has a length and a width and defines a volume that is less than the volume of the shell. At any point A1 and A2, between the in flow and the out flow, the catalyst bed has a length L1 such that between the out flow area and the in flow area over the catalyst bed length in between the out flow and the in flow, has an absolute ratio difference as expressed in (A2−A1)/L1 that is less than or equal to about 1.3M. Proximal to the out flow is fixed bed outlet zone 30 to minimize residence time of the effluent product material after exiting the catalytic bed. Generally, the fixed bed outlet zone is configured with an average residence time of less than or about 4 seconds for the gaseous product flow from the outlet of the catalyst bed to a heat exchanger to quench any undesired side reaction further converting alkylene oxide product to other unwanted byproducts such as $CO_2$, $H_2O$, carbon, and $CH_4$.

The catalyst may be selected from the group of catalysts with a lifetime selectivity higher than about 80%. Suitable catalysts may include, without limitation, a low selectivity catalyst such as SureCat® or a high selectivity catalyst such as Meteor®, both available from The Dow Chemical Company. When the catalyst bed is a low selectivity catalyst, the bed has a density in a range from about 960 kg/m³ to about 774 kg/m³, and if a high selectivity catalyst is used as the catalyst bed, the bed has a density in a range from about 837 kg/m³ to about 715 kg/m³.

The catalyst may be pills having a diffusion length from about 0.02 inches to about 0.07 inches, and more preferably, from about 0.025 inches to about 0.06 inches. The pill diffusion length can be determined by the ratio of the volume of a catalyst pellet to its exterior surface available for reactant penetration and diffusion. A more detailed definition and example can be found on page 476 of "Chemical Reaction Engineering", second edition, Wiley & Sons, 1972 incorporated in its entirety by reference. If a low selectivity catalyst is used, the preferred catalyst bed should have a length great than or equal to about 9.5 M, and if a high selectivity catalyst is used as the catalyst bed, the preferred bed should have a length greater than or equal to about 8.5 M.

Figure 1B:
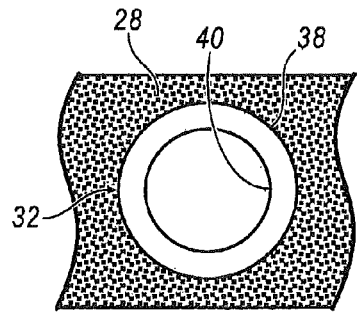
FIG. 1B is a cross sectional view of the heat transfer fluid enclosure of FIG. 1.

The reactor vessel is further equipped with a coolant fluid enclosure heat exchanger 32 having an inlet 34 and an outlet 36 for the circulation of heat transfer fluid through the vessel in a manner that may be parallel or cross wise to the direction of gaseous raw material flow through the catalyst bed. As seen in FIG. 1B, the coolant enclosure is generally designated as the coolant side of the reactor, and has an outer surface 38 in contact with the catalyst bed, and an inner surface 40, in contact with the heat transfer fluid. The coolant enclosure defines a coolant surface area with a heat transfer fluid flow cross sectional area ratio to the coolant surface area much less than 1. Moreover, the coolant enclosure surface area ratio to catalyst bed volume is preferably less than or equal to about 187 1/M. The heat transfer fluid may be boiling water in the coolant enclosure at a pressure of up to about 750 psig to maintain temperature in the catalyst bed at a temperature up to about 270° C. In addition, the pressure in the coolant side is preferably greater than the pressure on the process side of the reaction vessel.

Generally, the catalyst bed has an oxidation catalyst of a selectivity greater than about 80%, and, as previously stated, the flow of gaseous raw material through the catalyst bed may be parallel or cross to the direction of flow of heat transfer fluids in the heat transfer fluid enclosure. Accordingly, the coolant enclosure flow may be parallel, helical, perpendicular or in any other direction to the direction of flow of the gaseous raw material through the catalyst bed.

EXAMPLES

The following examples are offered to illustrate various aspects of the present invention. Those skilled in the art understand that they are not to be construed as limiting the scope and spirit of the invention. For all Figures discussed in the Examples, "XCSA" means cross flow catalyst-in-shell reactor; "GHSV" means Gas Hourly Space Velocity, "φ" means catalyst volume ratio; "SI" means calculated sensitivity index; "ΔP" means pressure drop and "STR" means conventional reactor with catalyst bed inside the tube.

Example 1

A comparison was made between a low selectivity (LS) ethylene oxide catalyst system, such as the Surecat® family and a high selectivity (HS) ethylene oxide catalyst system, such as the Meteor® family, both available from The Dow Chemical Company, with their relevant parameters particle diameter (Dp), porosity (ε), bed density ($\rho_B$), beginning of life (BOL) selectivity and typical end of life (EOL) selectivity. Table 1 lists some typical parameters for the low selectivity catalysts and the high selectivity catalysts.

TABLE 1

Parameters for low and high selectivity catalysts

| Case | Dp | ε | $\rho_B$ | Selectivity (BOL) | Selectivity (EOL) |
|---|---|---|---|---|---|
| Low Selectivity | 5.32 | 0.44 | 840 | 84 | 80 |
| High Selectivity | 6.84 | 0.44 | 776 | 92 | 88 |

Example 2

Figure 2A:
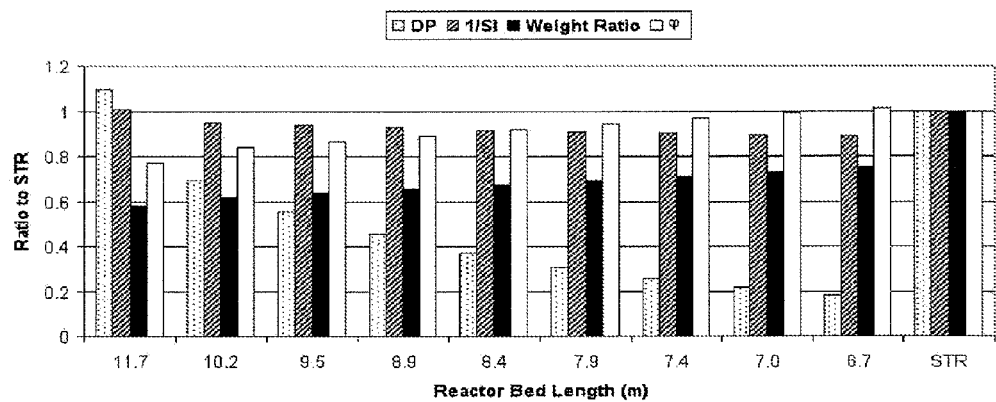
FIG. 2A is an evaluation of a catalyst-in-shell side reactor design with cross flow (XCSA) for a low selectivity catalyst with a GHSV of 5631 1/hr.

FIG. 2A is an evaluation of a catalyst-in-shell side reactor design with cross flow (XCSA) for low selectivity catalyst with GHSV of 5631 1/hr. A comparison case is shown with a 2" tube OD (1.83"ID) conventional shell and tube reactor with catalyst-in-tube (STR) design. For low selectivity (LS) catalysts with range of 80 to 86% such as disclosed in Example 1 above, a catalyst-in-shell with cross flow (XCSA) design with 0.75" coolant tube with GHSV of 5631 1/hr will show advantages over the conventional shell and tube reactor with catalyst-in-tube (STR) design with 2" tube OD (with 1.83" ID). The STR case tube ID is such that the heat transfer area over catalyst volume ratio (φ) is 86 1/M. In this case, the XCSA design will show improved stability as shown by the larger calculated sensitivity index (SI), lower weight and lower pressure drop (ΔP) and even lower φ with XCSA reactor bed length between 6.7 and 11.7 M as shown in FIG. 2A. It is also apparent that the ΔP decreases with a lower bed length while in contrast the reactor weight increases with lower bed length.

Figure 2B:
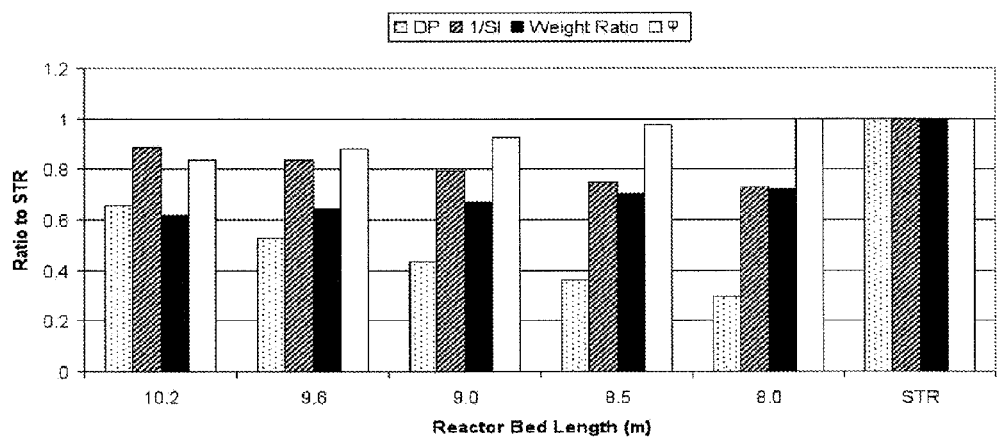
FIG. 2B is an evaluation of a catalyst-in-shell side reactor design with cross flow (XCSA) for a low selectivity catalyst with a GHSV of 7525 1/hr.

FIG. 2B is an evaluation of catalyst-in-shell side reactor design with cross flow (XCSA) for low selectivity catalyst with GHSV of 7525 1/hr. A comparison case is shown with 2" tube OD (1.83"ID) conventional shell and tube reactor with catalyst-in-tube (STR) design. The reactor of FIG. 2B will show a similar improvement as the reactor of FIG. 2A by using an XCSA concept with a GHSV of 7531 1/hr. Table 2 shows the detailed calculation results from LS catalyst and it also shows that similar improvement may be expected to be achieved in XCSA designs over STR designs using 2" OD tubes (φ=86 1/M and 1.83"ID) by using different coolant tubes OD while keeping the catalyst bed volume and other operating conditions (coolant temperature, GHSV, production rate, inlet pressure, inlet gas temperature) similar to STR cases and with SI, EO outlet concentration, and selectivity similar to or better than those in STR cases. In addition, Table 2 also shows that significant improvement in the φ (and thus reactor weight) may be obtainable at various coolant tube OD (e.g. XCSA 2, 5 and 8) while still providing lower ΔPs than that of STR cases. Note also that ΔP can be much lower than that in STR cases for various coolant tubes OD while still maintaining lower weight ratio (e.g. case XCSA 3, 6, and 9).

TABLE 2

Evaluation of catalyst-in-shell side reactor design with cross flow (XCSA) and comparison with conventional fixed bed reactor for lower selectivity catalyst for GHSV of 5631 1/hr.

| Case | STR | XCSA-1 | XCSA-2 | XCSA-3 | XCSA-4 | XCSA-5 | XCSA-6 | XCSA-7 | XCSA-8 | XCSA-9 |
|---|---|---|---|---|---|---|---|---|---|---|
| Φ (1/m) | 85.96 | 81 | 72.0 | 87.2 | 78.2 | 68.7 | 86 | 75.6 | 69 | 86 |
| coolant tube OD (in) | N/A | 0.75 | 0.75 | 0.75 | 1 | 1 | 1 | 1.25 | 1.25 | 1.25 |
| ΔP (psig) | 57.62 | 17.76 | 39.71 | 10.54 | 22.7 | 49.8 | 11.57 | 28 | 49.7 | 12.4 |
| Weight ratio | 1 | 0.69 | 0.62 | 0.75 | 0.69 | 0.61 | 0.76 | 0.68 | 0.62 | 0.76 |
| Ds ratio | 1 | 0.99 | 0.86 | 1.09 | 0.99 | 0.86 | 1.13 | 0.99 | 0.89 | 1.16 |
| L ratio | 1 | 0.69 | 0.89 | 0.58 | 0.75 | 0.96 | 0.6 | 0.85 | 0.95 | 0.61 |

Figure 2C:
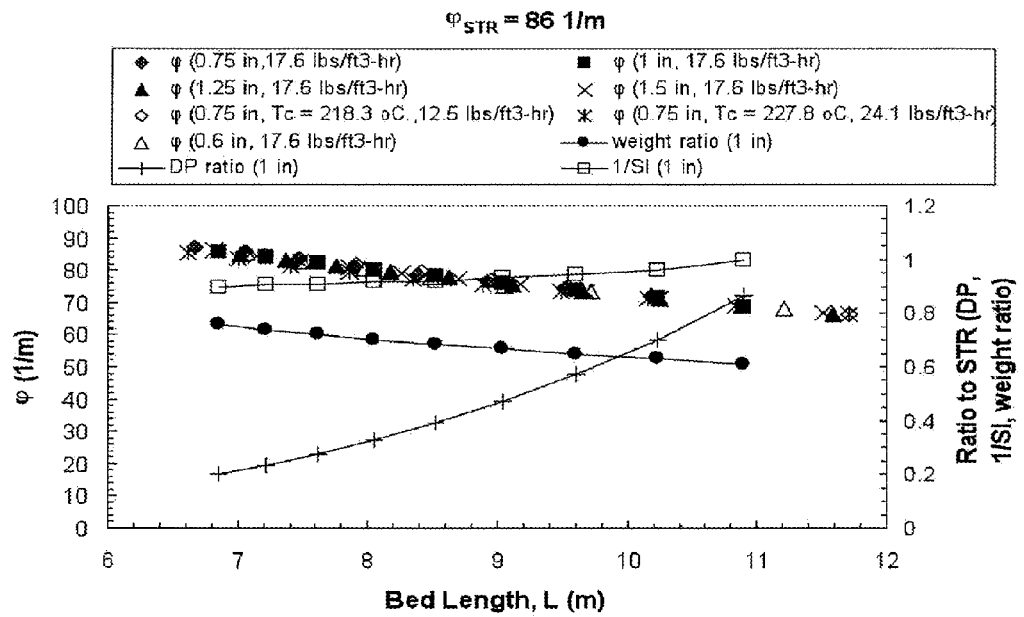
FIG. 2C is a plot of heat transfer area to catalyst volume ratio φ as function of reactor bed length for XCSA reactor designs with various coolant tube diameters and various coolant temperatures yielding different work rates for a low selectivity catalyst.

FIG. 2C is a plot showing the prediction of heat transfer area to catalyst volume ratio φ as a function of reactor bed length for XCSA reactor design with various coolant tube diameters and various coolant temperatures yielding different work rates (work rate is indicated in legend in lbs/ft$^3$-hr) for low selectivity catalyst. The ΔP, 1/SI and weight ratio with respect to STR cases (STR with 2" OD and $D_{ti}$=1.83") are also plotted as a function of bed length. FIG. 2C also shows the prediction that the XCSA design is advantageous over STR designs with $\varphi_{STR}$=86 1/M for different coolant temperatures and hence different production rates. More importantly, FIG. 2C also shows the prediction that the φ of XCSA design concept is always lower than or equal to $\varphi_{STR}$ of 86 1/M when the catalyst bed length is equal to or larger than 6.5 M. In addition, this is also predicted to be true for all coolant tubes OD of 0.6" to 1.5" and at various coolant temperatures. Note that FIG. 2C also demonstrates that the XCSA design can provide lower weight, higher stability, and lower ΔP with bed length up to about an 11 M bed than that of the STR design.

Figure 2D:
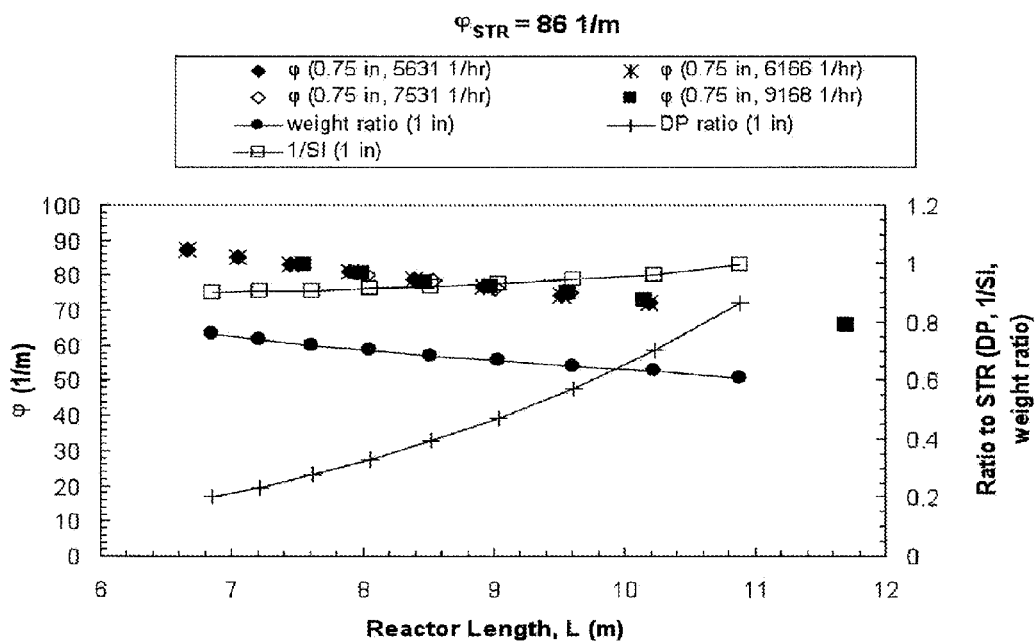
FIG. 2D is a plot of heat transfer area to catalyst volume ratio φ as function of reactor bed length for XCSA reactor designs at different GHSV values for a low selectivity catalyst.

FIG. 2D is plot showing prediction of heat transfer area to catalyst volume ratio φ as a function of reactor bed length for XCSA reactor design at different GHSV values for a low selectivity catalyst. The ΔP, 1/SI and weight ratio with STR cases (STR with 2" OD and $D_{ti}$=1.83") are also plotted as a function of bed length. FIG. 2D illustrates the predicted advantage of an XCSA design with lower φ for various GHSV values as compared to the STR case design with $\varphi_{STR}$=86 1/M. As shown above in reference to Table 2, both the predicted reactor ΔP and stability are also advantageous over an STR design of up to 11 M bed length.

Figure 2E:
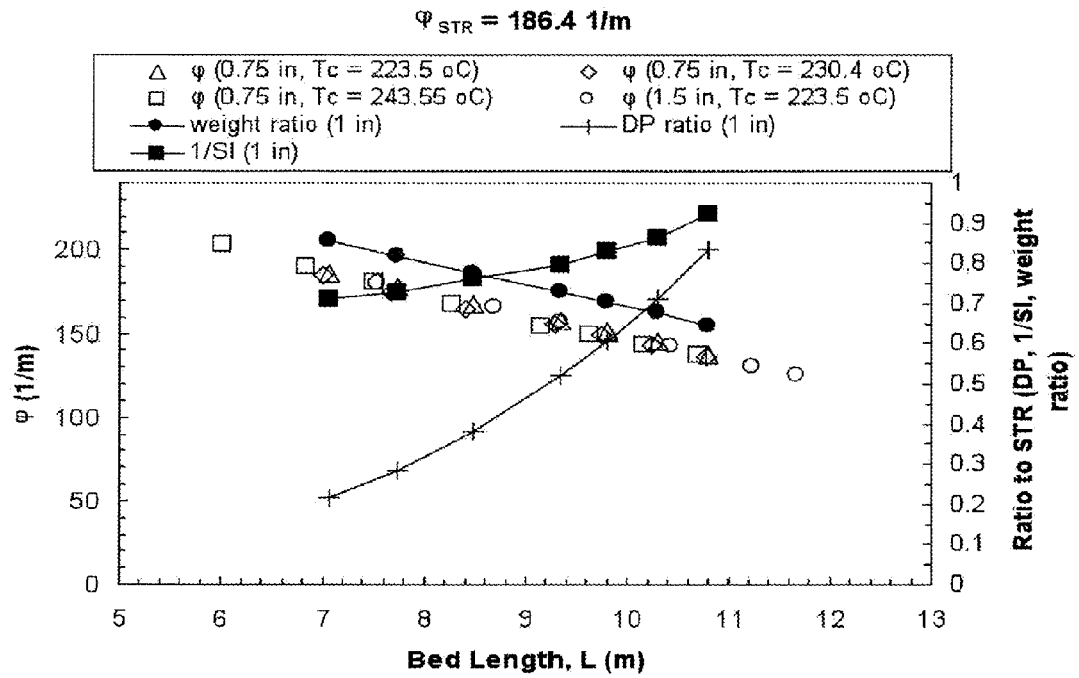
FIG. 2E is a plot of heat transfer area to catalyst volume ratio φ as function of reactor bed length for XCSA reactor designs with various coolant tube diameters and various coolant temperatures yielding different work rate for a low selectivity catalyst.

FIG. 2E is a plot showing a prediction of heat transfer area to catalyst volume ratio φ as a function of reactor bed length for XCSA reactor design with various coolant tube diameters and various coolant temperatures yielding different work rate (work rate is indicated in legend in lbs/ft$^3$-hr) for a low selectivity catalyst. The predicted ΔP, 1/SI and weight ratio with an STR case (conventional reactor with $D_{ti}$=0.84") are also plotted as a function of bed length. As is the case with FIGS. 2A through 2D, FIG. 2E demonstrates the predicted advantages of an XCSA design concept with lower φ as compared to the STR design with tube OD of 0.84" and $\varphi_{STR}$=186.4 1/M, at different coolant temperature and XCSA design coolant tube with OD of 0.75" and 1.5' with bed length in the range of 6.0 M to 12 M. This also illustrates that the XCSA design of FIG. 2E is expected to show better expected stability, requires lower expected reactor weight and ΔP at the operating conditions as STR with tube OD of 0.84" in the range of 6.5M to 11M bed length.

Figure 2F:
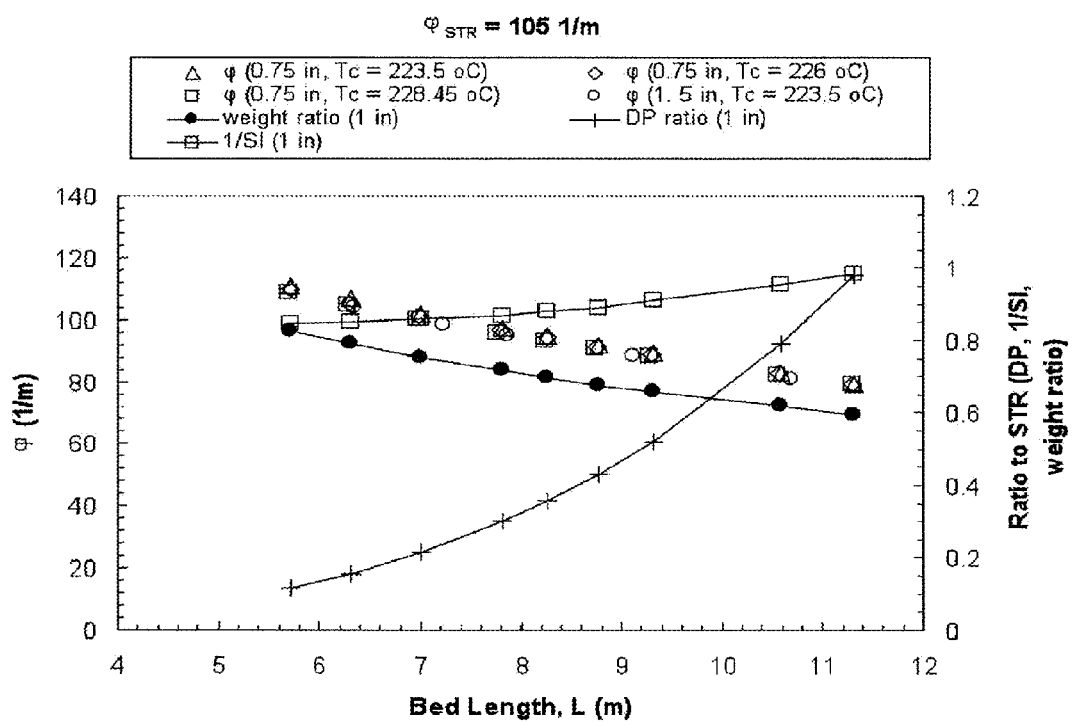
FIG. 2F is a plot of heat transfer area to catalyst volume ratio as function of reactor bed length for XCSA reactor designs with various tube diameters and various coolant temperatures yielding different work rate for a low selectivity catalyst.

FIG. 2F is a plot showing a prediction of heat transfer area to catalyst volume ratio as a function of reactor bed length for XCSA reactor design with various tube diameters and various coolant temperatures yielding different work rate (work rate is indicated in legend in lbs/ft$^3$-hr) for a low selectivity catalyst. The expected ΔP, 1/SI and weight ratio with STR case (conventional reactor with tube ID of 1.5") are also plotted as a function of bed length. A similar trend to that indicated in FIGS. 2A through E is illustrated in FIG. 2F for the XCSA design as compared to STR design case with tube ID of 1.5" and $\varphi_{STR}$=105.0 1/M, at different XCSA coolant tube ODs and coolant temperatures. FIG. 2F also depicts the expected XCSA advantageous bed length range of 5.8 M to 12.0 M.

Figure 2G:
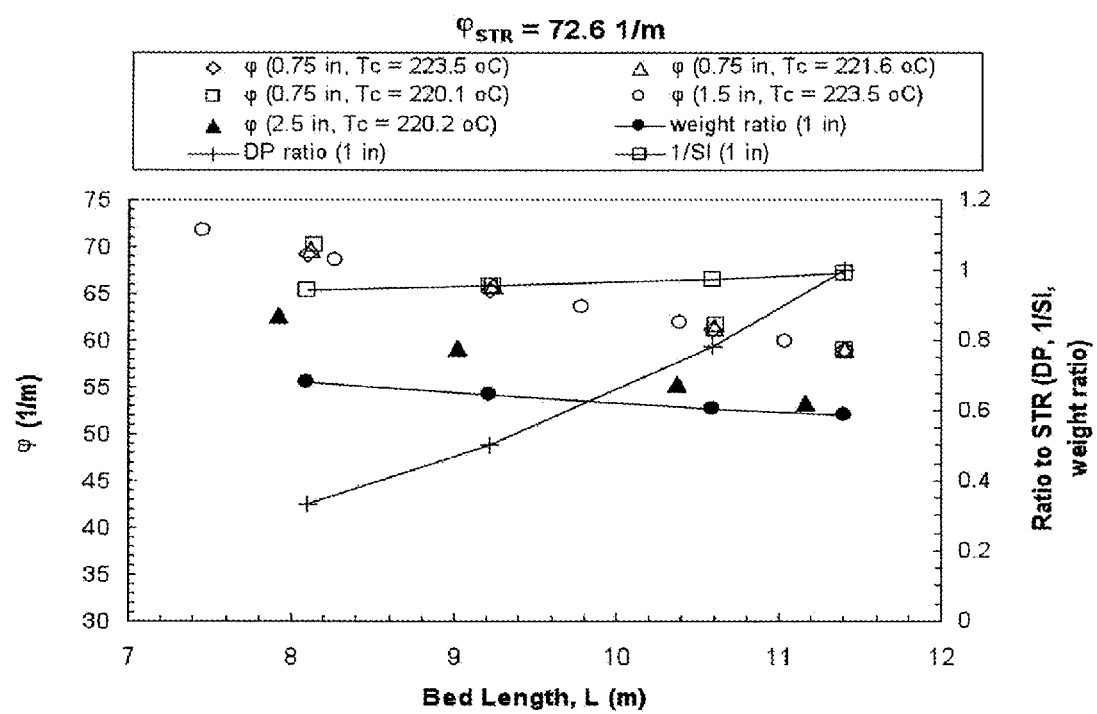
FIG. 2G is a plot of heat transfer area to catalyst volume ratio as function of reactor bed length for XCSA reactor designs with various tube diameters and various coolant temperatures yielding different work rate for a low selectivity catalyst.

FIG. 2G is a plot showing a prediction of heat transfer area to catalyst volume ratio as a function of reactor bed length for an XCSA reactor design with various tube diameters and various coolant temperatures yielding different work rate (work rate is indicated in legend in lbs/ft$^3$-hr) for a low selectivity catalyst. The expected ΔP, 1/SI and weight ratio with STR case (conventional reactor with tube ID of 2.17") are also plotted as a function of bed length. A similar trend as seen in FIGS. 2A through 2F is also illustrated in FIG. 2G for the XCSA design as compared to the STR case design with tube ID of 2.17" or $\varphi_{STR}$=72.6 1/M, at different coolant tube OD and coolant temperature. FIG. 2G also depicts the expected XCSA advantageous bed length range of 7.5 M to 11.5 M.

Figure 2H:
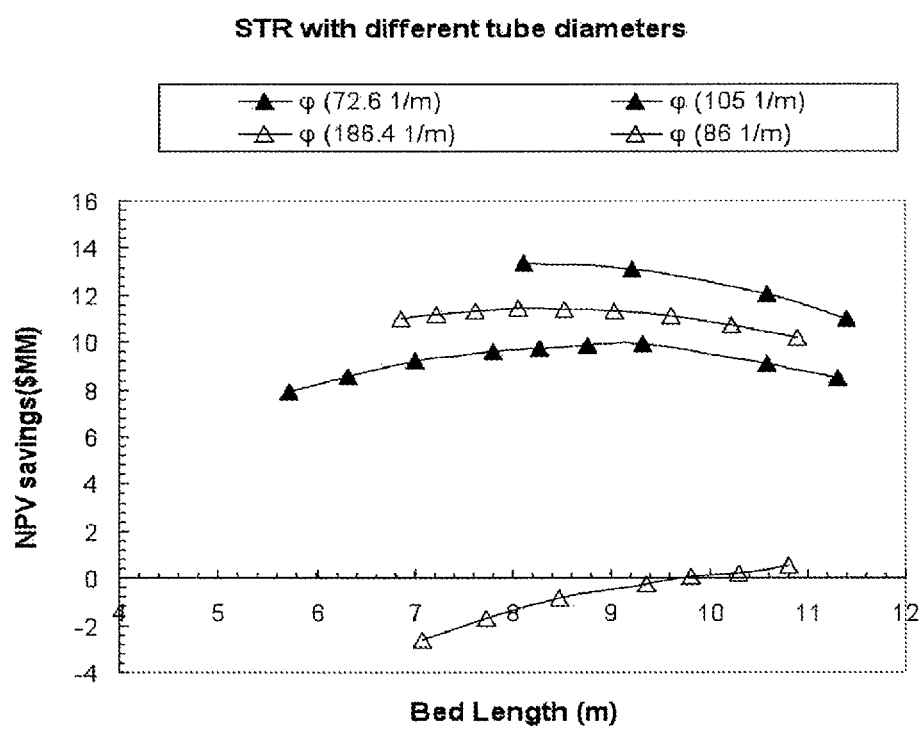
FIG. 2H is a plot of NPV savings of a feasible XCSA design with coolant tube as a function of bed length, as compared to an STR case with various heat transfer area ratios to catalyst volumes (or tube ID) for a low selectivity catalyst.

Finally, an expected overall net present value (NPV) improvement over the STR design of all the advantageous XCSA designs with various $\varphi_{STR}$ values is plotted against the bed length in FIG. 2H. The expected overall NPV improvement expected from savings in operating cost (Operating ΔP) and capital cost (approximately proportional to reactor weight) as compared to STR case with tube OD of 2", shows a maximum along the bed length range. For lower reactor bed lengths, NPV savings from operating costs are expected to increase, due to lower pressure drop across the reactor, and higher bed length savings from capital investment are expected to be higher due to lower reactor weight. This gives rise to the highest expected NPV savings at an intermediate length range from 8 to 9.5 M. More importantly FIG. 2H also shows that the expected NPV improvement of the XCSA design may begin to be realized for the case with $\varphi_{STR}$ of 186.4 1/M or tube OD of 0.84" in the STR design.

Example 3

Figure 3A:
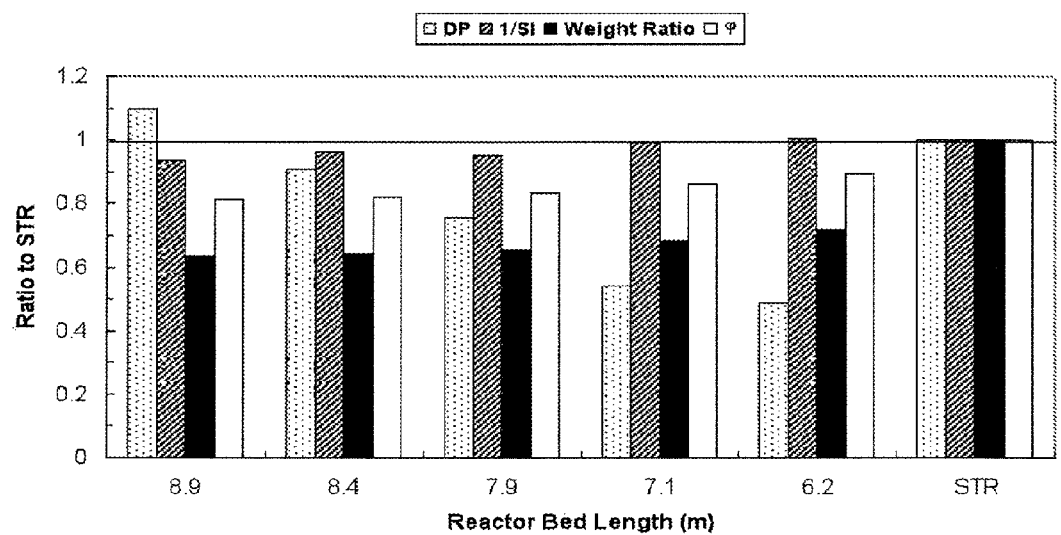
FIG. 3A is an evaluation of catalyst-in-shell side reactor design with cross flow (XCSA) for a high selectivity catalyst with a GHSV of 6652 1/hr.

FIG. 3A is a predicted evaluation of a catalyst-in-shell side reactor design with cross flow (XCSA) for a high selectivity catalyst with a GHSV of 6652 1/hr. The STR case is using a 2" tube OD (1.83"ID) for a conventional shell and tube reactor with catalyst-in-tube design. As depicted therein, for a high selectivity (HS) catalyst with range of 86 to 95%, the catalyst on the shell side with cross flow (XCSA) design with 0.75" coolant tube with GHSV 6652 1/hr is expected to show advantages over the conventional shell and tube reactor with catalyst-in-tube (STR) design with 2" tube OD (1.83"ID). The STR case has the same φ=86 1/M, as seen in Example 2. FIG. 3A depicts that the expected XCSA design requires lower φ than the STR design and also shows predicted improved stability, lower reactor weight and lower pressure drop (ΔP) with reactor bed length between 6M and 9M.

Figure 3B:
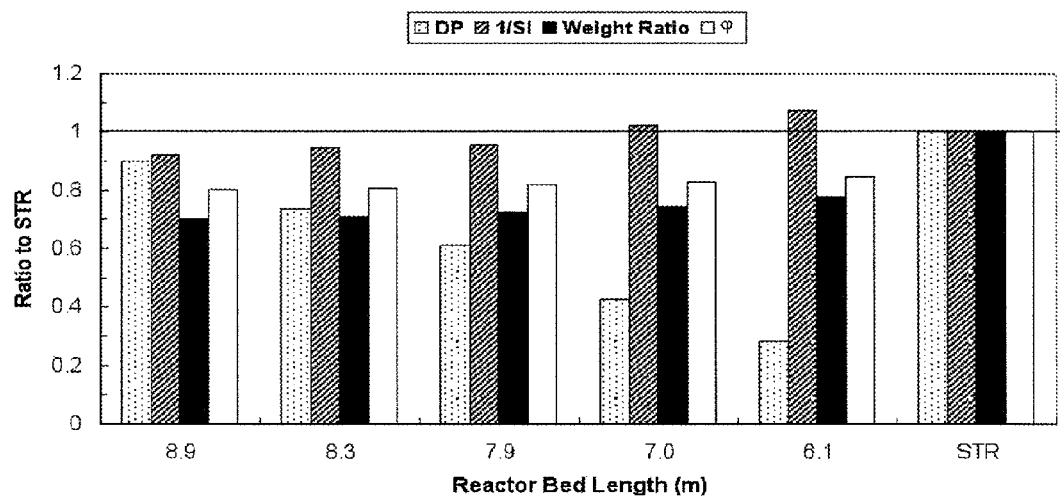
FIG. 3B is an evaluation of catalyst-in-shell side reactor design with cross flow (XCSA) for a high selectivity catalyst with a GHSV of 8500 1/hr.

Similar improvements are also expected for a case with different GHSV as shown in FIG. 3B. FIG. 3B is an evaluation of a predicted catalyst-in-shell side reactor design with cross flow (XCSA) for a high selectivity (HS) catalyst (Meteor) with a GHSV of 8500 1/hr. The STR case is with a 2" tube OD (1.83"ID) conventional shell and tube reactor with catalyst-in-tube design. Table 3 shows the detailed calculations expected results for HS catalyst and also shows that similar improvement can be expected to be achieved in an XCSA design over an STR design by using different coolant tube OD's while keeping catalyst volume and other operating conditions (coolant Temperature, GHSV, production rate, inlet pressure, inlet gas temperature) similar to the STR case. Table 3 also shows that significant improvement in the φ (thus reactor weight) is expected to be obtained at various coolant tube OD's (e.g. XCSA 2, 5 and 8) while still providing similar or lower ΔP than that of the STR case. Note that ΔP is expected to be much lower than that in STR case for various coolant tube OD while still maintaining lower weight ratio (e.g. case XCSA 1, 2, 6 and 7).

about 9.5 M as compared to an STR design. As shown above, both the predicted reactor ΔP and stability are also advantageous over an STR design up to 9.5 M bed length.

Figure 3C:
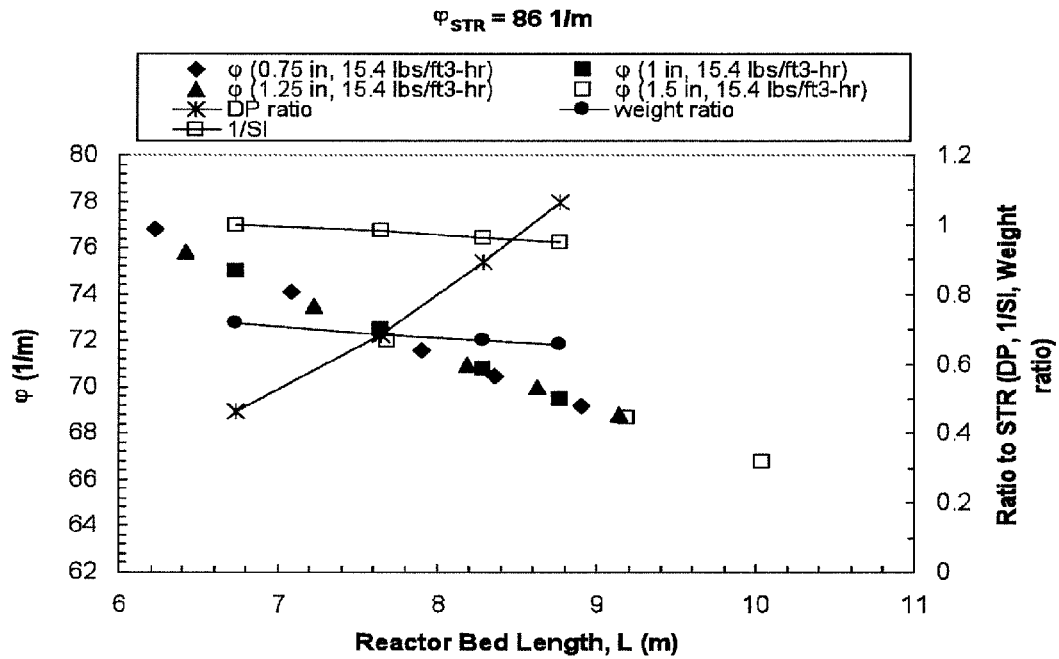
FIG. 3C is a plot of heat transfer area to catalyst volume ratio for high selectivity catalyst as a function of reactor bed length for XCSA reactor designs with various tube diameters.
Figure 3D:
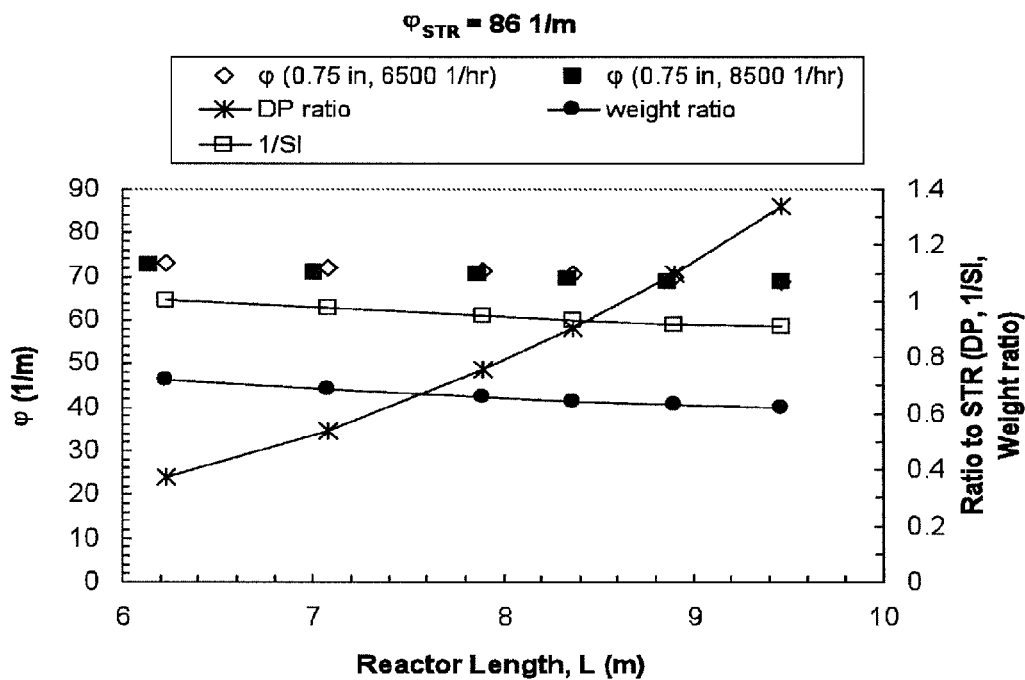
FIG. 3D is a plot of heat transfer area to catalyst volume ratio for a high selectivity catalyst as function of reactor bed length for XCSA reactor designs having different GHSV values.

FIG. 3D is a plot showing a prediction of heat transfer area to catalyst volume ratio as function of reactor bed length for an XCSA reactor design at different GHSV values. The expected ΔP, 1/SI and weight ratios with the STR case (conventional reactor with $D_{ti}$=1.83") are also plotted as a function of bed length for a high selectivity catalyst, such as Meteor. FIG. 3D illustrates the expected advantage of an XCSA design with lower φ for various GHSV values as compared to an STR case design with $\varphi_{STR}$=86 1/M. As shown above, both the expected reactor ΔP and stability are also advantageous over an STR design up to 9.5 M bed length.

Figure 3E:
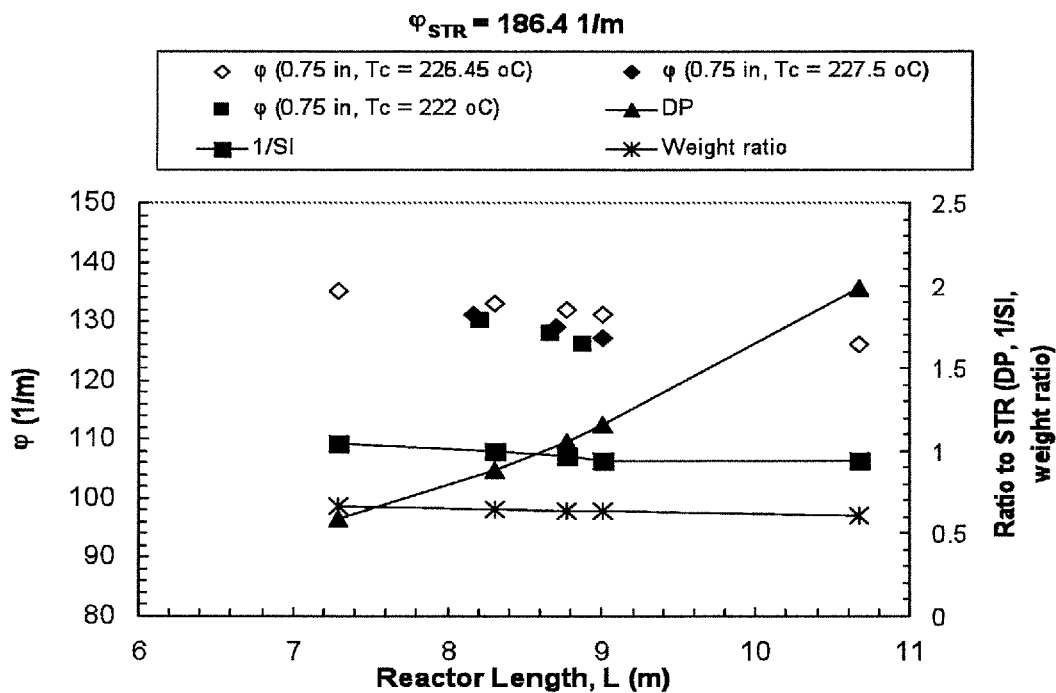
FIG. 3E is a plot of the heat transfer area to catalyst volume ratio as function of reactor bed length for XCSA reactor designs with various coolant temperatures yielding different work rate for a high selectivity catalyst.

FIG. 3E is a plot showing a prediction of heat transfer area to catalyst volume ratio as function of reactor bed length for an XCSA reactor design with various coolant temperatures yielding different work rate for a high selectivity catalyst. Work rate is indicated in legend in lbs/ft$^3$-hr. The expected ΔP, 1/SI and weight ratio with an STR case (conventional reactor with tube ID of 0.84") are also plotted as a function of bed length. FIG. 3E is similar to FIGS. 3A through 3D, and demonstrates the predicted advantages of an XCSA design concept with lower φ as compared to an STR case design with tube OD of 0.84" and $\varphi_{STR}$=186.4 1/M, at different coolant temperature and design coolant tubes with OD of 0.75" with bed length in the range of 7.5 M to 9.0 M. FIG. 3E also illustrates that the XCSA design shows better expected stability, requires lower reactor weight and ΔP at the same operating conditions as an STR with tube OD of 0.84" in the range of 7.5 to 9.8 M bed length.

Figure 3F:
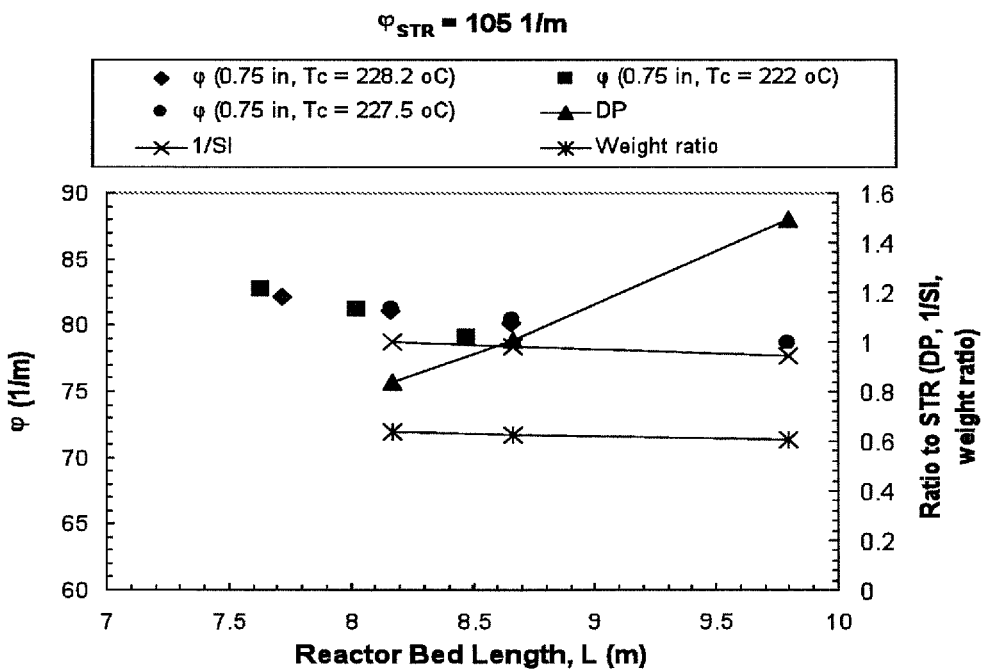
FIG. 3F is a plot of heat transfer area to catalyst volume ratio as function of reactor bed length for XCSA reactor designs with various coolant temperatures yielding different work rate for a high selectivity catalyst.

FIG. 3F is a plot showing a prediction of heat transfer area to catalyst volume ratio as a function of reactor bed length

TABLE 3

Catalyst-in-shell side reactor designs with cross flow (XCSA) and comparison with conventional fixed bed reactor for high selectivity catalyst with GHSV of 6652 1/hr.

| Case | STR | XCSA-1 | XCSA-2 | XCSA-3 | XCSA-4 | XCSA-5 | XCSA-6 | XCSA-7 | XCSA-8 | XCSA-9 |
| --- | --- | --- | --- | --- | --- | --- | --- | --- | --- | --- |
| Φ, Heat transfer/cat vol (1/M) | 86 | 76 | 70 | 86.0 | 75 | 71 | 72.5 | 75 | 69 | 76 |
| coolant tube OD (in) | N/A | 0.75 | 0.75 | 0.75 | 1 | 1 | 1 | 1.25 | 1.25 | 1.25 |
| ΔP (psig) | 37.7 | 29.9 | 41.5 | 15 | 14.52 | 33.45 | 21.48 | 18.43 | 37.28 | 12.59 |
| Weight ratio | 1 | 0.68 | 0.63 | 0.77 | 0.71 | 0.66 | 0.68 | 0.72 | 0.65 | 0.74 |
| Ds ratio | 1 | 0.88 | 0.83 | 1.00 | 1 | 0.87 | 0.93 | 1.00 | 0.88 | 1.07 |
| L ratio | 1 | 0.93 | 1.03 | 0.74 | 0.78 | 1.02 | 0.89 | 0.84 | 1.05 | 0.74 |

FIG. 3C is a plot showing a prediction of heat transfer area to catalyst volume ratio for high selectivity catalyst as a function of reactor bed length for an XCSA reactor design with various tubes. Work rate is indicated in legend in lbs/ft$^3$-hr. The expected ΔP, 1/SI and weight ratio with STR case tube OD's of 2" (ID of 1.83") are also plotted as a function of bed length. FIG. 3C shows that various XCSA designs are expected to be advantageous over an STR design with $\varphi_{STR}$=86 1/M for different coolant temperatures and hence different production rates. FIG. 3C also shows that the φ of an XCSA design concept is always lower than or equal to $\varphi_{STR}$ of 86 1/M when bed length is equal to or larger than 6.2 M and this is valid for all coolant tubes OD of 0.75" to 1.5" and at various coolant temperatures. FIG. 3C also demonstrates that an XCSA design concept is expected to have lower weight, stability, and ΔP up to a bed length of for an XCSA reactor design with various coolant temperatures yielding different work rates for a high selectivity catalyst. Work rate is indicated in legend in lbs/ft$^3$-hr. The expected ΔP, 1/SI and weight ratio with the STR case (conventional reactor with tube ID of 1.5") are also plotted as a function of bed length. FIG. 3F is similar to FIGS. 3A through 3E, and sets forth the predicted advantages of an XCSA design as compared to an STR design case with tube ID of 1.5" and $\varphi_{STR}$=105 1/M, at different XCSA coolant temperatures. FIG. 3F also depicts the XCSA is expected to have an advantageous bed length range of 7.8 M to 9.0 M.

Figure 3G:
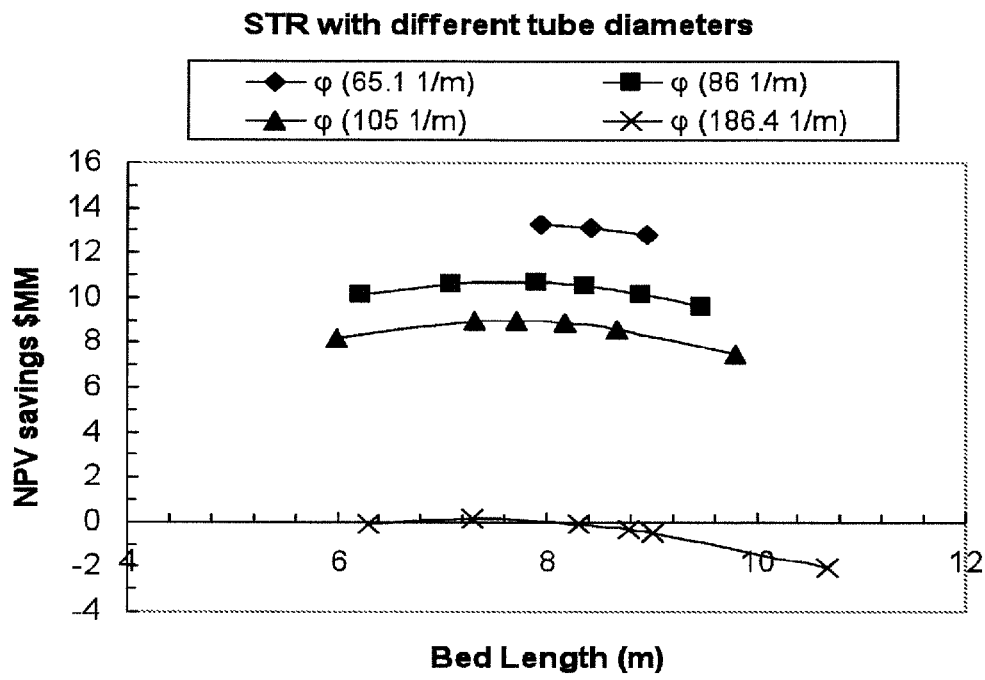
FIG. 3G is a plot of NPV savings of feasible XCSA designs with coolant tubes OD of 0.75" as a function of bed length, as compared to an STR case with various heat transfer area ratio to catalyst volume (or tube ID) for a high selectivity catalyst.

FIG. 3G is a plot of predicted NPV savings of a feasible XCSA design with coolant tube OD of 0.75" as a function of bed length, as compared to an STR case with various heat transfer area ratio to catalyst volume (or tube ID) for a high selectivity catalyst. The expected overall net present value (NPV) improvement over the STR design of all the advantageous XCSA designs with various $\varphi_{STR}$ values are plotted against the bed length in FIG. 3G for the high selectivity catalyst system. The expected overall NPV improvement coming from savings in operating cost (proportional to the operating $\Delta P$) and capital cost (proportional to the reactor weight) as compared to base case STR with tube OD of 2", shows a maximum along the bed length range. For lower reactor bed length, expected NPV savings from operating costs are higher as seen in FIG. 3G, and for higher bed length, predicted savings from capital investments are higher due to lower reactor weight, as seen in FIG. 3F. This gives rise to a highest expected NPV at an intermediate length range from 7.0 to 8.5 m. More importantly FIG. 3G also shows that the NPV improvement of the XCSA design may be expected to be realized for the case with $\varphi_{STR}$ of 186.4 1/M or tube OD of 0.84" in the STR design.

Example 4

Figure 4:
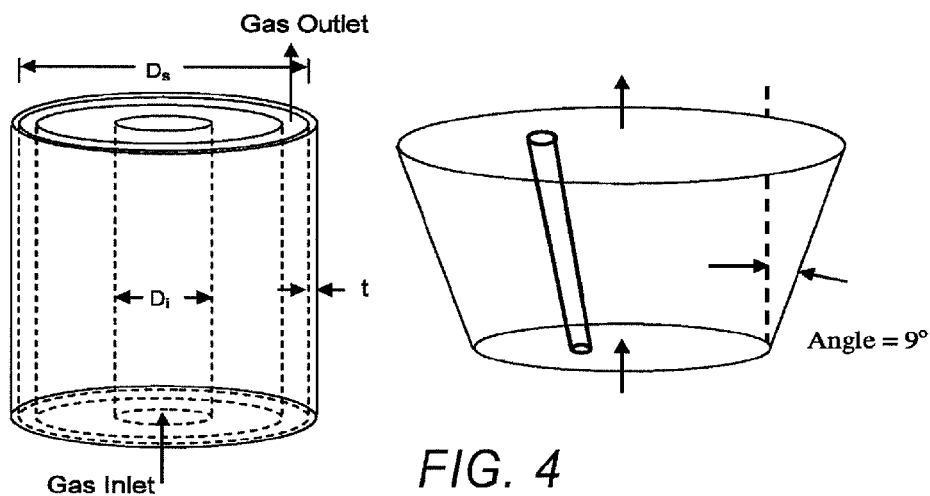
FIG. 4 is a schematic of radial flow reactor and cone shaped catalyst bed reactor designs.

This example illustrates the predicted impact of a reactor catalyst bed with varying areas in the direction of process flow. The ratio of the absolute difference between outlet and inlet area over the catalyst bed length $A_L$ of less than 1.3 M indicates where the reactor could be operated with sufficient stability. For a tubular type of reactor this can be represented with a truncated cone shape catalyst bed with an angle of 9° as shown in FIG. 4. This 9° angle represents the predicted expansion in the shell and tubes such that heat transfer area to catalyst volume is maintained at 67 (1/M). When $A_L$ is larger than 1.3 M as is the case in the radial flow reactor as shown in Table 5, the reaction is predicted to run away since the flow rate would decrease with bed length and reduce the heat transfer rate.

TABLE 5

Design variables of radial flow design and variable area design at constant catalyst volume with coolant tube OD of 0.75" and $\varphi$ = 67 1/M.

| Case | Radial Flow Design | Varying area axial flow design (9°) | Radial Flow Design |
| --- | --- | --- | --- |
| Bed length, L (M) | 5.5 | 6.4 | 4.5 |
| $D_i$ for Radial design (M) | 1 | N/A | 2 |
| $A_L$ (M) | 19.2 | 1.3 | 18.9 |

Example 5

Figure 5A:
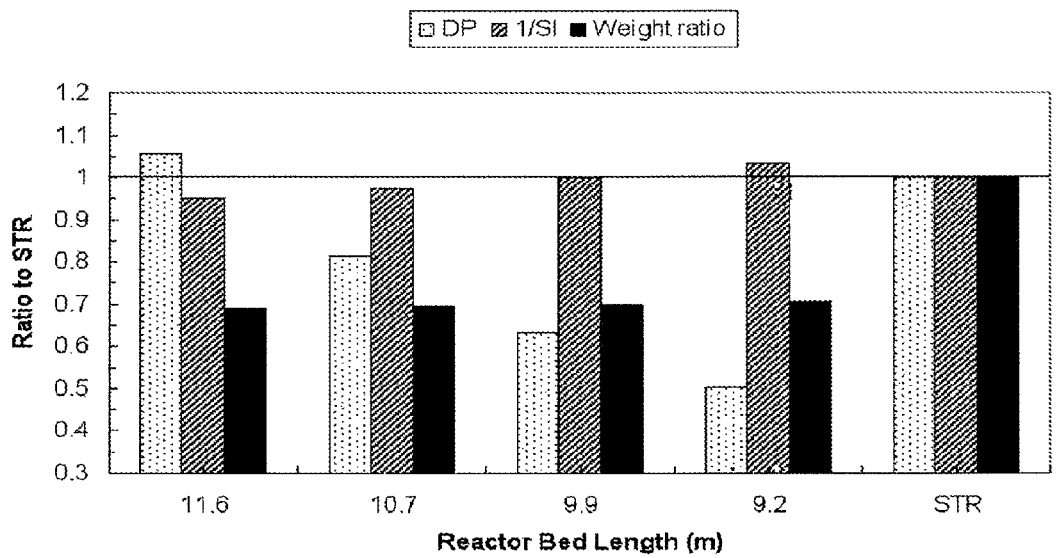
FIG. 5A is an evaluation of catalyst-in-shell side axial flow designs with flow parallel to the coolant carrier (CSA) for low selectivity catalyst as compared to an STR case.
Figure 5B:
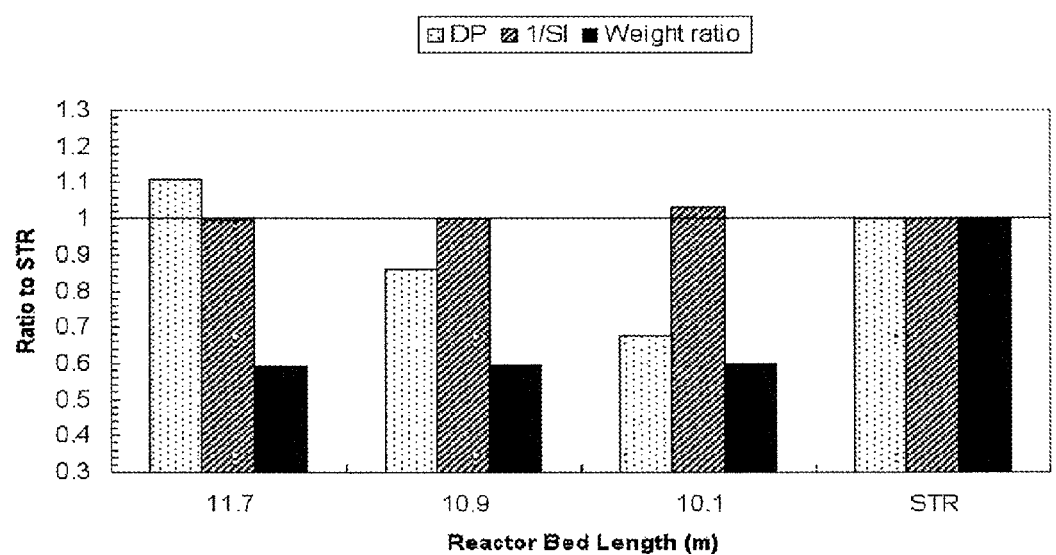
FIG. 5B is an evaluation of catalyst-in-shell side axial flow designs with flow parallel to the coolant carrier (CSA) for low selectivity catalyst as compared to an STR case.

FIG. 5A shows the predicted feasible catalyst-in-shell design with reactant gas flowing parallel (CSA) to the heat transfer surface area with LS catalyst (e.g. Surecat® family as seen Example 1) with a coolant tube OD of 0.75". This case is compared with a 2" tube OD (1.83"ID) conventional shell and tube reactor with catalyst-in-tube (STR) design. The heat transfer area to catalyst volume required for the CSA design is expected to be the same as the STR case ($\varphi$=86 1/M). The cross flow configuration (XCSA) is expected to provide better heat transfer than the CSA design with lower $\varphi$ values (lowest $\varphi$ value required for XCSA design is 22% lower than the STR case). The heat transfer coefficient for the XCSA design with cross flow configuration is predicted to be almost twice that of the CSA design. The wider feasible catalyst-in-shell design window for the XCSA design is expected to be achieved with a bed length in the range of 6.7-11 M as compared to the CSA design with a bed length range of 9-11 M. This may be seen in a comparison of FIG. 2A and FIG. 5A. The expected minimum $\Delta P$ for the XCSA design is 80% lower than the STR case, as compared to expected minimum $\Delta P$ for the CSA design, which is only 50% lower than the STR case. The predicted minimum reactor weight for the feasible XCSA design is 42% lower than the STR case as compared to the predicted minimum reactor weight for CSA design, which is 31% lower than the STR case. Similarly, FIG. 5B also shows the expected advantages of the CSA design with coolant tube OD of 1" as compared to the STR case. The overall expected performance of the XCSA design is better than the CSA design with lower $\varphi$ values, lower $\Delta P$, lower reactor weight and better reactor stability.

Example 6

Figure 6A:
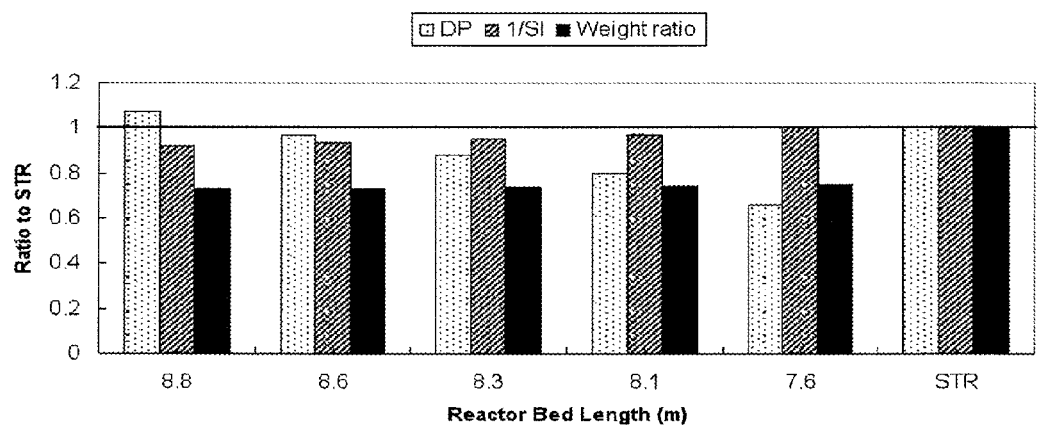
FIG. 6A is an evaluation of catalyst-in-shell side axial flow designs with flow parallel to the coolant carrier (CSA) for high selectivity catalyst as compared to an STR case.

FIG. 6A shows the predicted feasible catalyst-in-shell design with reactant gas flowing parallel (CSA) to the heat transfer surface area with HS catalyst (e.g. Meteor family as seen in example 1) with a coolant tube OD of 0.75". The heat transfer area to catalyst volume required for the CSA design is the same as the STR case ($\varphi$=86 1/M). The cross flow configuration of the predicted XCSA provides better heat transfer than a CSA design with lower $\varphi$ values. Note that the lowest expected $\varphi$ value required for the XCSA design is 20% lower than the STR case. The heat transfer coefficient for an XCSA design with cross flow configuration is predicted to be almost twice that of a CSA design. The wider feasible catalyst-in-shell design window for an XCSA design may be achieved with a bed length in the range of 6.0-9 M as compared to a CSA design with a bed length range of 7.6-8.8 M. This can be seen in a comparison of FIG. 3A and FIG. 6A. The expected minimum $\Delta P$ for an XCSA design is 50% lower than the STR case, as compared to the predicted minimum $\Delta P$ for the CSA design, which is only 37% lower than the STR case. The expected minimum reactor weight for the feasible XCSA design is 37% lower than the STR case as compared to predicted minimum reactor weight for CSA design, which is 27% lower than the STR case. The STR case depicted is with a 2" tube OD (1.83"ID) conventional shell and tube reactor with catalyst-in-tube (STR) design.

Figure 6B:
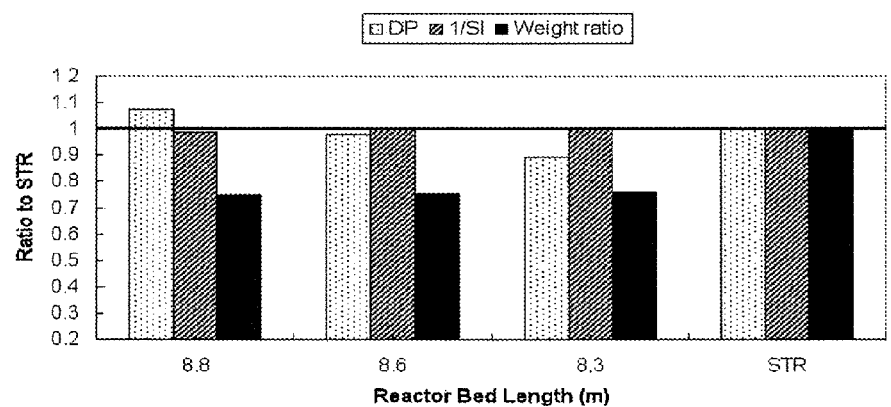
FIG. 6B is an evaluation of catalyst-in-shell side axial flow designs with flow parallel to the coolant carrier (CSA) for high selectivity catalyst as compared to STR case.

FIG. 6B is an evaluation of a predicted catalyst-in-shell side axial flow design with flow parallel to the coolant carrier (CSA) for high selectivity catalyst as compared to the STR case. As is the case with FIG. 6A, FIG. 6B shows the expected advantages of a CSA design with coolant tube OD of 1" as compared to the STR case. The overall performance of the XCSA design is predicted to be better than the CSA design with lower $\varphi$ values, lower $\Delta P$, lower reactor weight and better reactor stability.

Example 7

Figure 7:
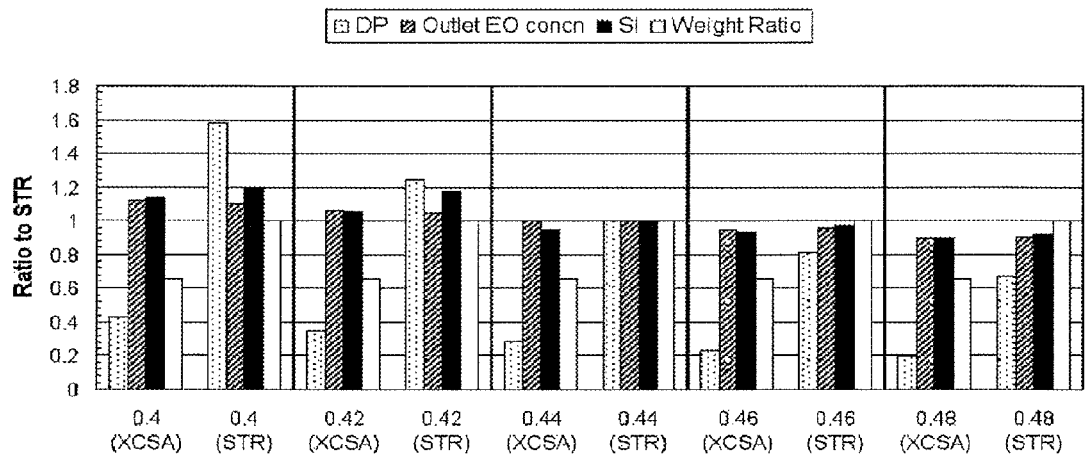
FIG. 7 shows the comparison of XCSA reactor designs and conventional reactor designs performance of various ranges of catalyst bed porosity and density for low selectivity catalyst.

The expected porosity and catalyst bed density effect on low selectivity EO catalyst system with XCSA design is shown in FIG. 7. The porosity ($\epsilon$) is varied from 0.4 to 0.48 as compared to typical value of 0.44. FIG. 7 shows that for all the porosity ranges and the corresponding catalyst bed density ranges, the XCSA design is expected to always perform better than the corresponding STR case with lower $\Delta P$, lower reactor weight, and better stability. The predicted preferred range of catalyst bed porosity is within 0.43-0.45.

Example 8

Figure 8:
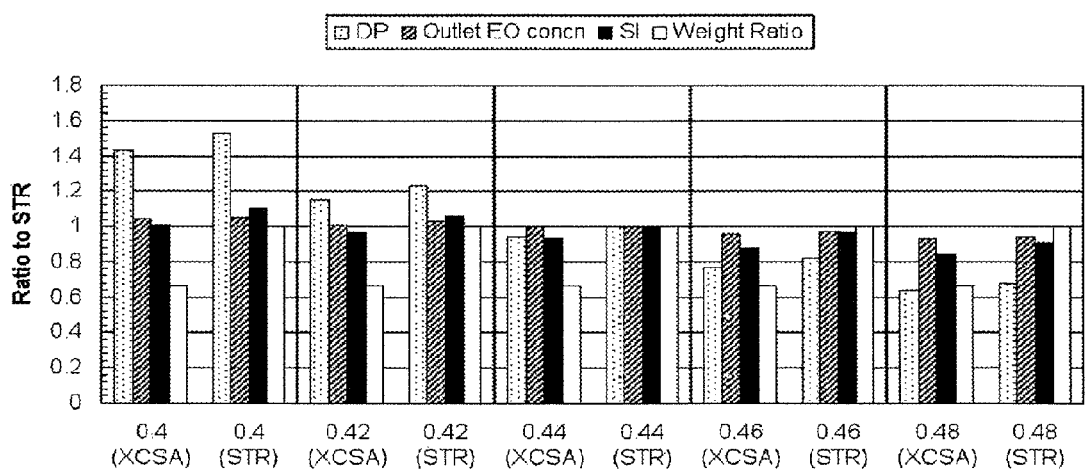
FIG. 8 shows the comparison of an XCSA and conventional reactor designs performance for various ranges of catalyst bed porosity and density for a high selectivity catalyst.

The predicted effect of porosity and catalyst bed density on a high selectivity EO catalyst system with an XCSA design is shown in FIG. 8. The porosity (ϵ) is varied from 0.4 to 0.48 as compared to a typical value of 0.435. FIG. 8 shows that for all the porosity ranges and the corresponding catalyst bed density ranges, the XCSA design is always predicted to perform better than the conventional STR case with lower ΔP, lower reactor weight, and better reactor stability. The expected preferred range of catalyst bed porosity is within 0.42-0.44.

Those skilled in the art recognize that the words used in this specification are words of description and not words of limitation. Many variations and modifications will be apparent to those skilled in the art upon a reading of this application without departing from the scope and sprit of the invention as set forth in the appended claims.

The invention claimed is:

1. A reaction vessel comprising:
a shell having an inflow and an outflow; the shell with a length and width to define a reactor vessel interior volume;
a catalyst bed shape defined by the reactor vessel interior volume, the catalyst bed having a length such that an out flow area and an in flow area over the catalyst bed length in between the reactor outflow and inflow has an absolute ratio difference less than or equal to about 1.3 meter anywhere in the catalyst bed; the catalyst bed defining a process side and having a length less than the shell length and a volume less than the shell volume; a fixed bed outlet zone-configured for a gaseous flow through the catalyst bed to a heat exchanger to quench the reactions; the catalyst bed forming a process side of the reaction vessel; and
at least one coolant enclosure heat exchanger in the shell interior volume to define a coolant side of the reaction vessel, the coolant enclosure having an outside surface and an inside surface to define a heat transfer fluid flow path, the coolant enclosure outside surface in contact with the catalyst, the coolant enclosure having an inlet and an outlet for flow of heat transfer fluid through the coolant enclosure inner surface; the coolant enclosure further defining a cooling surface area with the coolant flow cross sectional area ratio to a cooling surface area being much less than 1.

2. The reaction vessel of claim 1, wherein the coolant enclosure cross sectional area is at least equivalent to one tube having an inner diameter of 0.2 inches to 1.8 inches.

3. The reaction vessel of claim 1, wherein the absolute ratio difference is 0.8 meter to 1.3 meter.

4. The reaction vessel of claim 1, wherein a flow direction of gaseous alkylene through the catalyst bed is parallel to a direction of the heat transfer fluid flow through the coolant enclosure.

5. The reaction vessel of claim 1, wherein the catalyst is comprised of pills having a diffusion length of 0.02 inches to 0.07 inches.

6. The reaction vessel of claim 1, wherein the catalyst bed length is larger than 8.5 meter.

7. The reaction vessel of claim 1, wherein the catalyst bed length is larger than 9.5 meter.

8. The reaction vessel of claim 1, wherein the catalyst bed has a porosity in a range of from about 0.38 to about 0.49.

* * * * *